(12) United States Patent
Nadershahi et al.

(10) Patent No.: US 9,050,048 B2
(45) Date of Patent: Jun. 9, 2015

(54) MINIMALLY OBSTRUCTIVE RETRACTOR

(75) Inventors: Afshin Nadershahi, Northridge, CA (US); Ricardo Hahn, Ojai, CA (US); Carrie Nichols, Newport Beach, CA (US); Kelly Jones, Norwalk, CA (US); Sudeep Deshpande, Los Angeles, CA (US)

(73) Assignee: ALFRED E. MANN INSTITUTE FOR BIOMEDICAL ENGINEERING AT THE UNIVERSITY OF SOUTHERN CALIFORNIA, Los Angeles, CA (US)

( * ) Notice: Subject to any disclaimer, the term of this patent is extended or adjusted under 35 U.S.C. 154(b) by 758 days.

(21) Appl. No.: 13/248,928

(22) Filed: Sep. 29, 2011

(65) Prior Publication Data

US 2012/0083658 A1 Apr. 5, 2012
US 2012/0209076 A2 Aug. 16, 2012
US 2013/0041229 A2 Feb. 14, 2013

Related U.S. Application Data

(60) Provisional application No. 61/387,863, filed on Sep. 29, 2010, provisional application No. 61/436,119, filed on Jan. 25, 2011.

(51) Int. Cl.
*A61B 1/32* (2006.01)
*A61B 17/02* (2006.01)
(Continued)

(52) U.S. Cl.
CPC ............... *A61B 1/32* (2013.01); *A61B 17/0218* (2013.01); *A61B 17/42* (2013.01); *A61B 2017/00407* (2013.01); *A61B 2017/00849* (2013.01); *A61B 2019/521* (2013.01)

(58) Field of Classification Search
CPC .......... A61B 1/32; A61B 1/303; A61B 17/02; A61B 17/0206; A61B 17/0218; A61B 17/0212; A61B 17/0225; A61B 17/0237; A61B 17/0243; A61B 17/42; A61B 17/4241
USPC .................................................. 600/201-246
See application file for complete search history.

(56) References Cited

U.S. PATENT DOCUMENTS 361,087 A 4/1887 Schenck
639,444 A 12/1899 Scheerer
(Continued)

FOREIGN PATENT DOCUMENTS

CN 1863479 A 11/2006
CN 101287404 A 10/2008
(Continued)

OTHER PUBLICATIONS

Official Action, dated May 15, 2014, from the Patent Office of the Russian Federation, for counterpart Russian Application No. 2013119383, entitled "Minimally Obstructive Retractor," national phase filing in Russia based on WO 2012/047725 (with translation and redacted cover sheet provided by Russian counsel, showing receipt date).

(Continued)

*Primary Examiner* — Christian Sevilla
*Assistant Examiner* — Eric S Gibson
(74) *Attorney, Agent, or Firm* — McDermott Will & Emery LLP

(57) ABSTRACT

This application presents minimally-obstructive and structurally-adjustable retractors which afford an open work area of desirable size and enhanced visualization for a surgeon about the perineum and the posterior vaginal wall of the patient. The retractors may be lightweight and compact, and also configured and dimensioned to minimize slippage during use. The retractors may retract the engorged labia of the postpartum patient as well as the vaginal walls. The device may also be used as a speculum.

53 Claims, 17 Drawing Sheets

(51) Int. Cl.
*A61B 17/42* (2006.01)
*A61B 17/00* (2006.01)
*A61B 19/00* (2006.01)

(56) References Cited

U.S. PATENT DOCUMENTS

| | | | |
|---|---|---|---|
| 761,821 A | 6/1904 | Clark et al. | |
| 786,457 A | 4/1905 | McGinnis | |
| 1,014,799 A | 7/1914 | Arthur | |
| 2,374,863 A | 5/1945 | Guttmann | |
| 3,176,682 A | 4/1965 | Wexler | |
| 3,736,919 A * | 6/1973 | Cotey | 600/225 |
| 3,745,992 A * | 7/1973 | Poirier | 600/225 |
| 3,774,596 A | 11/1973 | Cook | |
| 3,796,214 A | 3/1974 | Davis | |
| 4,447,227 A | 5/1984 | Kotsanis | |
| 5,183,032 A * | 2/1993 | Villalta et al. | 600/224 |
| 5,626,129 A * | 5/1997 | Klimm et al. | 128/202.22 |
| 5,643,285 A | 7/1997 | Rowden et al. | |
| 5,785,648 A * | 7/1998 | Min | 600/206 |
| 5,868,668 A * | 2/1999 | Weiss | 600/224 |
| 6,024,696 A | 2/2000 | Hoftman et al. | |
| 6,024,697 A | 2/2000 | Pisarik | |
| 6,048,308 A | 4/2000 | Strong | |
| 6,196,969 B1 * | 3/2001 | Bester et al. | 600/224 |
| 6,302,842 B1 | 10/2001 | Auerbach et al. | |
| 6,364,832 B1 | 4/2002 | Propp | |
| 6,416,467 B1 * | 7/2002 | McMillin et al. | 600/224 |
| 6,432,048 B1 | 8/2002 | Francois | |
| 6,450,952 B1 * | 9/2002 | Rioux et al. | 600/223 |
| 6,595,917 B2 | 7/2003 | Nieto | |
| 6,599,292 B1 * | 7/2003 | Ray | 606/90 |
| 7,060,029 B1 * | 6/2006 | Hajianpour | 600/190 |
| 7,141,015 B2 | 11/2006 | Ruane | |
| 7,175,594 B2 | 2/2007 | Foulkes | |
| 7,481,766 B2 | 1/2009 | Lee et al. | |
| 7,594,888 B2 * | 9/2009 | Raymond et al. | 600/219 |
| 8,734,337 B2 * | 5/2014 | Deitch et al. | 600/220 |
| 8,808,175 B2 * | 8/2014 | Deitch et al. | 600/220 |
| 2004/0116777 A1 * | 6/2004 | Larson et al. | 600/210 |
| 2005/0113644 A1 * | 5/2005 | Obenchain et al. | 600/222 |
| 2005/0215862 A1 | 9/2005 | Larson et al. | |
| 2008/0228038 A1 | 9/2008 | McMahon et al. | |
| 2009/0076334 A1 * | 3/2009 | Chen | 600/223 |
| 2009/0099422 A1 | 4/2009 | George | |
| 2009/0326331 A1 | 12/2009 | Rosen | |
| 2011/0021879 A1 * | 1/2011 | Hart et al. | 600/207 |
| 2012/0083658 A1 * | 4/2012 | Hahn et al. | 600/205 |
| 2012/0209076 A2 * | 8/2012 | Hahn et al. | 600/205 |
| 2012/0232352 A1 * | 9/2012 | Lin et al. | 600/220 |
| 2013/0041229 A2 * | 2/2013 | Hahn et al. | 600/205 |

FOREIGN PATENT DOCUMENTS

| | | | |
|---|---|---|---|
| CN | 101433452 A | | 5/2009 |
| DE | 19828099 A1 | | 12/1999 |
| SU | 167005 A1 | | 1/1965 |
| SU | 1509048 A1 | | 9/1989 |
| WO | 02054961 A1 | | 7/2002 |
| WO | 2004002322 A1 | | 1/2004 |
| WO | 2004098416 A2 | | 11/2004 |
| WO | 2005016131 A2 | | 2/2005 |
| WO | 2006107878 A2 | | 10/2006 |
| WO | WO 2007075903 A2 * | | 7/2007 |
| WO | 2009099543 A2 | | 8/2009 |
| WO | 2012047725 A1 | | 4/2012 |

OTHER PUBLICATIONS

Extended European Search Report, dated Jul. 23, 2014, from the European Patent Office, for counterpart European Application No. 11831346.9, entitled "Minimally Obstructive Retractor," European Regional Phase filing based on WO 2012/047725.

International Search Report and Written Opinion of International Searching Authority for PCT Application No. PCT/US2011/054064, filed Sep. 29, 2011, entitled "MInimally Obstructive Retractor," published Apr. 12, 2012 as WO 2012/047725 A1.

Weber et al. 2002. Episiotomy Use in the United States, 1979-1997, Obstetrics & Gynecology, pp. 1177-1182, vol. 100, No. 6.

Leeman et al. 2003. Repair of Obstetric Perineal Lacerations, American Family Physician, pp. 1586-1590, vol. 68, No. 8.

Frankman et al. 2009. Episiotomy in the United States: has anything changed?, Am J Obstet Gyncol, vol. 200, pp. 573.e1-573.e7.

Cooper Surgical Inc., Guardian Vaginal Retractor, 2009, two pages.

Office Action, dated Jan. 12, 2015, for Chinese Application No. 201180047230.8, entitled "Minimally Obstructive Retractor," Chinese national phase of PCT/US2011/054064, PCT counterpart to U.S. Appl. No. 13/248,928.

International Search Report and Written Opinion of the US International Searching Authority (ISA/US), dated Dec. 18, 2014, for PCT Application No. PCT/US2014/052573, entitled "Minimally Obstructive Retractor for Vaginal Repairs," filed Aug. 25, 2014.

International Search Report and Written Opinion of the US International Searching Authority (ISA/US), dated Dec. 30, 2014, for PCT Application No. PCT/US2014/052574, entitled "Speculum for Obstetrical and Gynecological Exams and Related Procedures," filed Aug. 25, 2014.

* cited by examiner

MINIMALLY OBSTRUCTIVE RETRACTOR

CROSS-REFERENCE TO RELATED APPLICATIONS

This application is related, and claims priority, to U.S. Provisional Patent Application Ser. No. 61/387,863, filed Sep. 29, 2010, entitled "Minimally Obstructive Surgical Retractor and Speculum"; and U.S. Provisional Patent Application Ser. No. 61/436,119, filed Jan. 25, 2011, entitled "Minimally Obstructive Retractor;" the entire contents of both of which are incorporated herein by reference.

TECHNICAL FIELD

This invention relates generally to medical surgical instruments, particularly structurally-adjustable retractors and speculums for gynecological examinations and operations.

BACKGROUND

Devices which have been proposed for the purpose of vaginal examination and gynecological surgical procedures may not be entirely satisfactory for a variety of reasons. In many cases, they may obstruct the vision of the deep internal parts of the vaginal cavity that they are intended to expose. They may also constrain the movement of the physicians' hands and reduce the open work area for the surgeon. This often reduces the efficiency and effectiveness of vaginal examinations and surgical procedures.

Furthermore, typically the vagina walls, the perineum (which is the area of tissue between the vagina and the anus), and the anus are torn during vaginal delivery. Natural perineal tears are classified by their severity. First-degree tears involve tearing only the skin. Second-degree tears involve tearing muscle. Third-degree tears involve tearing the external anal sphincter muscle. Fourth-degree tears further involve tearing the rectal mucosa. When fourth-degree tears occur, the mother may require post-birth surgery to stitch up the torn tissue, often under general anesthetic.

Sometimes the perineum is purposely cut by a doctor performing an episiotomy, which is an incision into the perineum to enlarge the size of the vaginal opening. An episiotomy is similar to a first or second-degree natural tear.

All of the above tearing or incisions usually require post-delivery operations to stitch up the area. Stitching fourth-degree tears is particularly difficult using known specula given that fourth-degree tears typically extend from the vagina wall all the way to the rectum. Such surgery is extremely difficult due to the flaccid nature of the surrounding tissue which exists immediately after birth.

Episiotomy retractors for retracting friable postpartum vaginal tissue to facilitate repair of the episiotomy or vaginal laceration are known. The primary function of the retractor is to provide an open work area for the surgeon about the perineum and posterior vaginal wall of the patient so that the surgeon can conveniently and safely approximate and suture the tissue planes to complete repair.

The known episiotomy retractors may not be entirely satisfactory in use. Existing speculums may not permit access to the area in which the stitching is required and furthermore may tend to interfere with the surgeons ability to make the stitches in the first place.

Most importantly, conventional retractors may fail to provide sufficient open work area for the surgeon about the perineum and the posterior vaginal wall of the patient. During the delivery process the labia of the patient may become engorged with blood and thus may tends to interfere with visualization of the desired work area by the surgeon.

Furthermore, conventional retractors often include scissor arms or other elongated portions for gripping and leverage. However, these elements may increase the size and cost of the devices, and can constrain the movement of the physicians' hands and reduce the open work area for the surgeon.

SUMMARY

This application presents minimally obstructive retractors and speculums that afford an open work area of desirable size and enhanced visualization to users about the perineum and the posterior vaginal wall of the patient. The retractor may be lightweight, and configured and dimensioned to minimize slippage during use. The position of various elements of the device may be adjusted prior to, during, and after the procedure. The device may retract the engorged labia of the postpartum patient as well as the vaginal walls. The retractor may be simple and inexpensive to manufacture, use and maintain.

The device may provide several benefits, including but not limited to: permitting two-handed surgical techniques, facilitating approximation of tissue layers, retaining its angle of retraction, preventing fluids and tissues from obstructing the posterior vaginal wall and perineum, and promoting hemostasis.

The device may be used for improved visualization, access, and repair in various procedures, including, but not limited to: obstetrical/gynecological procedures: vaginal inspection; perineal inspection; vaginal wound repair; perineal wound repair; episiotomy repair; female pelvic exam; pap smear; cervical biopsy; vaginal/pelvic reconstruction; urological procedures; colorectal, general, or other surgery; the device may be turned upside-down, for example, for female urologic procedures; access to the cervix (or uterus via cervix); IUD insertion, removal, or adjustment; and dilatation & curettage (dilatation of cervix and curettage of uterus).

The minimally obstructive retractor has a proximal end and a distal end, and an exterior surface and an interior surface. In one embodiment, this retractor may comprise a central body portion, at least two wings, and at least two hinges, each configured to affix a different one of the at least two wings to the central body portion. The central body portion, the at least two wings, and the at least two hinges form a canopy.

In another embodiment, this canopy is formed such that the fluid flow through the exterior surface of the canopy, defined by the exterior surfaces of the body, wings and hinges, is substantially blocked. In an example of this embodiment, the hinges may be living hinges.

The minimally obstructive retractor may further comprise protruded portions, thinned portions, or combinations thereof. Such protruded or thinned portions may be formed on the exterior surface of the central body portion, the wing, or both the central body portion and the wing.

The minimally obstructive retractor may also comprise a ratchet mechanism. This ratchet mechanism may have one arm that is affixed to the interior surface of at least one wing.

Furthermore, in one embodiment, the retractor may further comprise a gripping proximal tip at the proximal end. Also, the retractor may further comprise a retractor limiter at the proximal end.

In some embodiments, the minimally obstructive retractor may further comprise an illumination source. This illumination source may comprise at least one light-emitting diode. In one embodiment, the illumination source may be located within the canopy. In another embodiment, the light emitting diode may be located within the canopy. Yet, in another embodiment, the illumination source is automatically turned on in conjunction with movement of the ratchet arms away from each other and/or automatically turned off in conjunction with movement of the ratchet arms towards each other.

In other embodiments, the hinge may comprise polyethylene, polypropylene, nylon, acetal plastics or a mixture thereof. The hinge may also comprise polyethylene, polypropylene, or a mixture thereof.

In an embodiment, the retractor may further comprise a lubrication source comprising a lubricant-containing reservoir integrated to the retractor and configured to provide lubricant to an outer surface of the retractor.

It is understood that other embodiments of the devices and methods will become readily apparent to those skilled in the art from the following detailed description, wherein it is shown and described only exemplary embodiments of the devices, methods and systems by way of illustration. As will be realized, the devices, systems and systems are capable of other and different embodiments and its several details are capable of modification in various other respects, all without departing from the spirit and scope of the invention. Accordingly, the drawings and detailed description are to be regarded as illustrative in nature and not as restrictive.

BRIEF DESCRIPTION OF THE DRAWINGS

Aspects of the minimally obstructive retractor are illustrated by way of example, and not by way of limitation, in the accompanying drawings.

DETAILED DESCRIPTION

Figure 1:
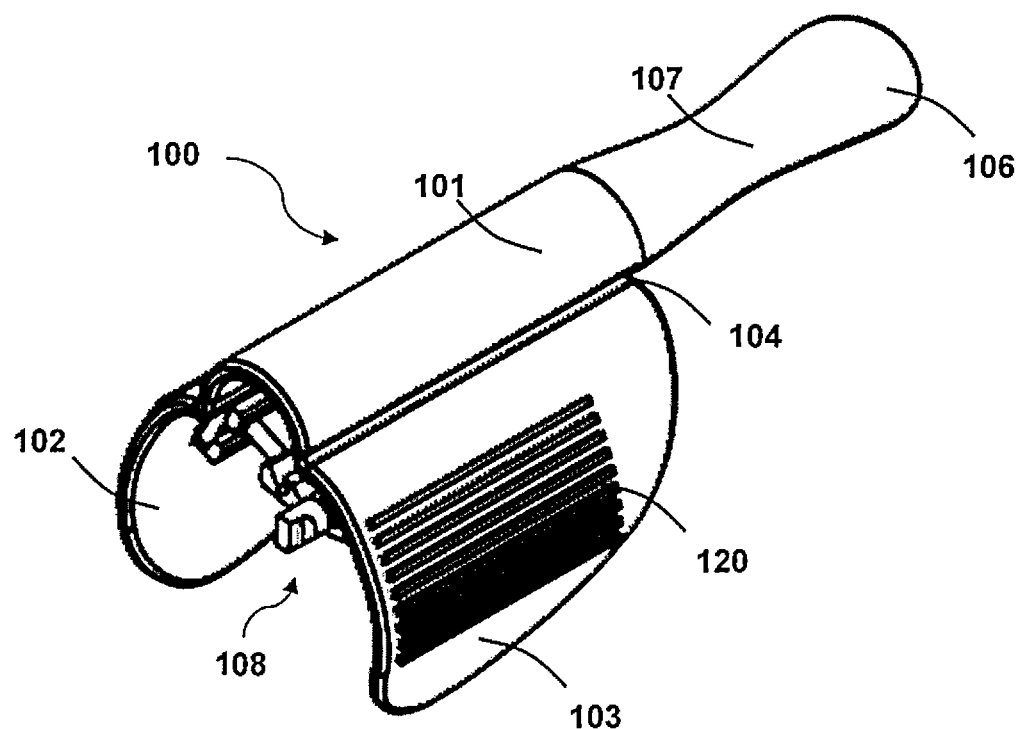
FIG. 1 is an isometric view of an exemplary retractor.
Figure 2:
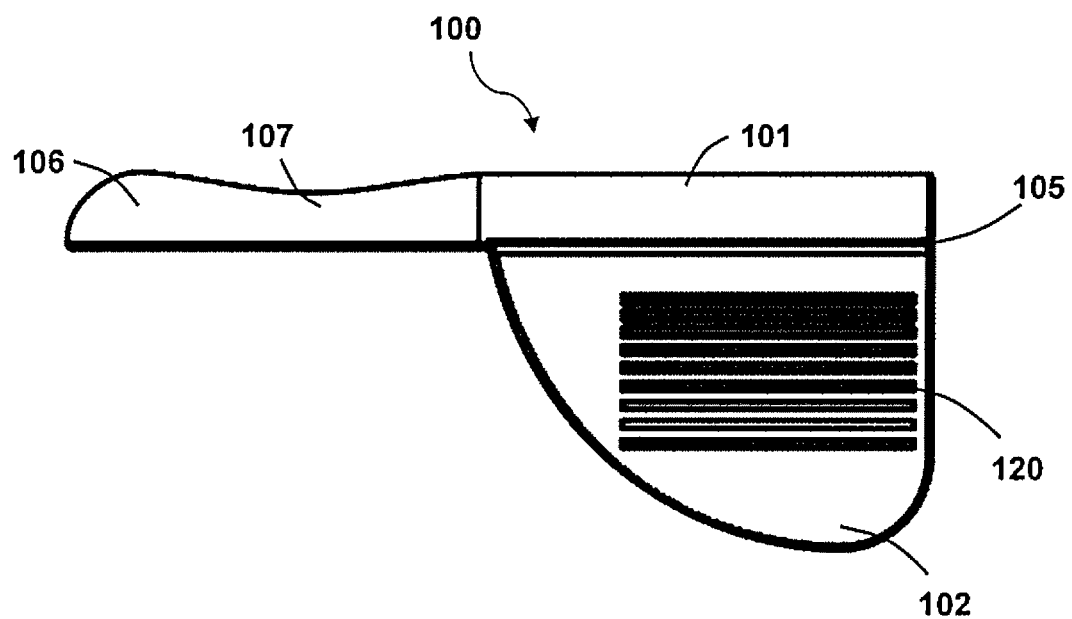
FIG. 2 is a side view of the exemplary retractor of FIG. 1.
Figure 3:
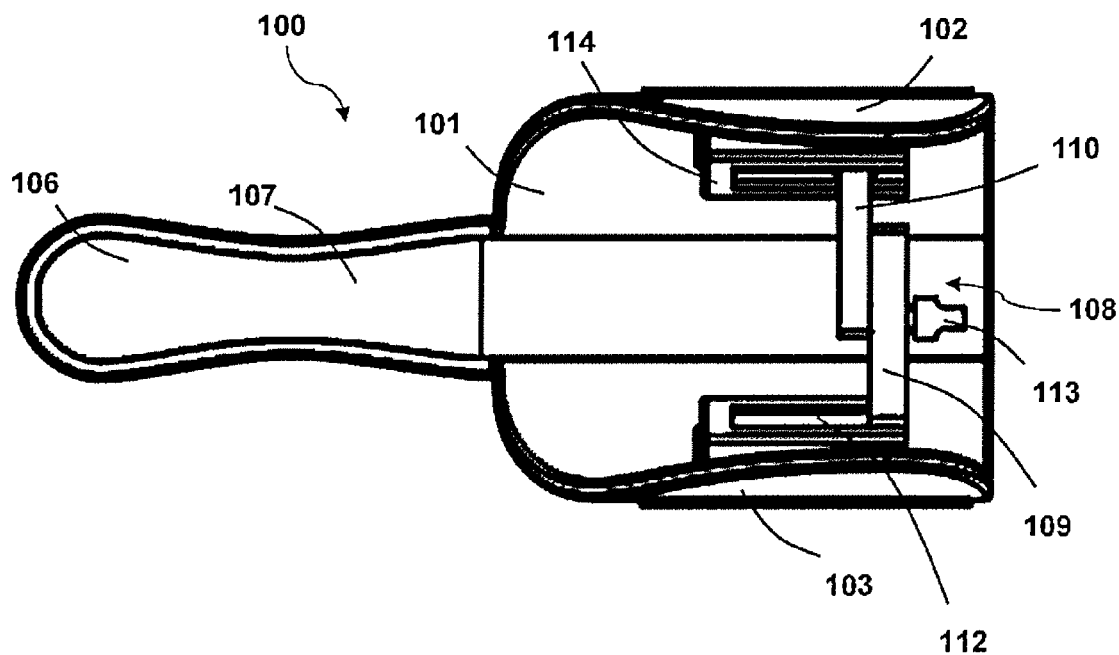
FIG. 3 is a bottom view of the exemplary retractor of FIG. 1.

The detailed description set forth below in connection with the appended drawings is intended as a description of exemplary embodiments and is not intended to represent the only embodiments in which the retractors and speculums can be practiced. The term "exemplary" used throughout this description means "serving as an example, instance, or illustration," and should not necessarily be construed as preferred or advantageous over other embodiments. The detailed description includes specific details for the purpose of providing a thorough understanding of the retractors/speculums. However, it will be apparent to those skilled in the art that the retractors/speculums and may be practiced without these specific details.

This invention relates generally to medical surgical instruments, particularly structurally-adjustable retractors and speculums for gynecological examinations and operations. These medical devices are hereafter called "minimally obstructive retractors" or "retractors."

The minimally obstructive retractor has a proximal end and a distal end. This retractor may comprise a central body portion, at least two wings, and at least one hinge configured to affix at least one wing to the central body portion. The central body portion, the at least one wing, and the at least one hinge may form a canopy.

In some embodiments, the canopy may be formed such that the fluid flow through the exterior surface of the canopy, defined by the exterior surfaces of the body, wings and hinges, is substantially blocked. An example of this embodiment comprises a so-called "living hinge". In this example, the retractor may be formed as one piece, by using manufacturing techniques such as molding, machining or welding. And the thinned section of the retractor, which is relatively thinner than the central body portion and the wings, forms the living hinge. Thereby, the one-piece retractor can easily flex along the line of the living hinge. A hinge of this type may be capable of many flexures over an extended period of time without the material fatiguing or breaking.

In one embodiment, the width of the living hinge is smaller than the width of the wing and/or the central body portion. In another embodiment, the living hinge width is substantially smaller than the width of the wing and/or the central body portion.

The living hinge is not the only retractor example that has a canopy wherein the fluid flow through the exterior surface of the canopy is substantially blocked. Other examples are as follows. In one example, a retractor may be formed by substantially reducing the width of the hinge and/or the width of the gap between the central body portion and the wing. In another example, the wings are formed to overlap on the exterior surface of the central body portion or the central body portion is formed to overlap on the exterior surface of the wings. Yet, in another example, the retractor may further comprise a substantially impermeable membrane that substantially covers the exterior and/or the interior surface of the canopy, or the exterior and/or the interior surface of the gap between the central body portion and the wings.

The wing has a proximal end and a distal end. The wing also has a top adjacent to the hinge and a bottom.

FIGS. 1-4 depict various views of an exemplary minimally obstructive retractor (100). The exemplary device (100) comprises wings (102, 103). These wings may be solid. These wings may also be hollow and shell-like to provide a convex exterior and conversely, a generally concave interior to permit visual as well as manual access thereto. The wings may be of a shape, contour, thickness, angle, radius, and size to hold up the vaginal walls during various procedures.

The wings (102, 103) may be affixed to a central body portion (101). The central body portion (101) may be convex on the exterior of the device (100) and concave on the interior. The central body portion (101) may be of a shape, contour, thickness, angle, radius, and size to hold up the vaginal walls during various procedures.

The wings (102, 103) may be connected to the central body portion (101) by hinges (104, 105). The hinges (104, 105)

may comprise the same or different material as the wings (102, 103) and the central body portion (101). The hinges (104, 105) may permit the wings (102, 103) to flex or pivot about the central body portion (101) such that the lower longitudinal wing edges of the retractor may be pivoted open to permit visual and manual access to the interior of a body passage.

The wings (102, 103) may also comprise protruded and/or thinned portions (120, 121) to provide friction and prevent the device (100) from undesirable movement during use. These thinned portions are thinner than the remaining portions of the wing. The protruded and/or thinned portions (120, 121) may protrude from the wings (102, 103) or be etched or carved into the wings. The protruded and/or thinned portions may be anywhere on the wings. The protruded and/or thinned portions may comprise various shapes or forms such as grooves, serrations, cross-hatches, bumps, or other morphologies to provide adequate friction with the tissue, while not damaging the tissue or causing discomfort to the patient. In other embodiments, the top portion of the central body portion (101) may comprise grooves, blunted barbs, or other textures to provide friction and to resist slippage of the device within the vaginal cavity. In one exemplary embodiment, the wings comprise serrated wing edges. This serrated wing edges may be at the bottom.

The exemplary device (100) may also comprise a distal tip (106), which is the first part of the device inserted into the body. The distal tip (106) may be thick and wide enough to hold the upper portion of the vaginal walls during various procedures. The distal end of the distal tip (106) may be round and smooth to provide comfort and minimize damage to the tissue during use. The distal tip (106) may also comprise a concave portion (107) that facilitates insertion into the body and provides better contact with the tissue by conforming to the body structure. In some embodiments, the distal tip (106) may also comprise grooves, blunted barbs, or other textures to provide friction and to resist slippage of the device within the vaginal cavity.

Figure 4:
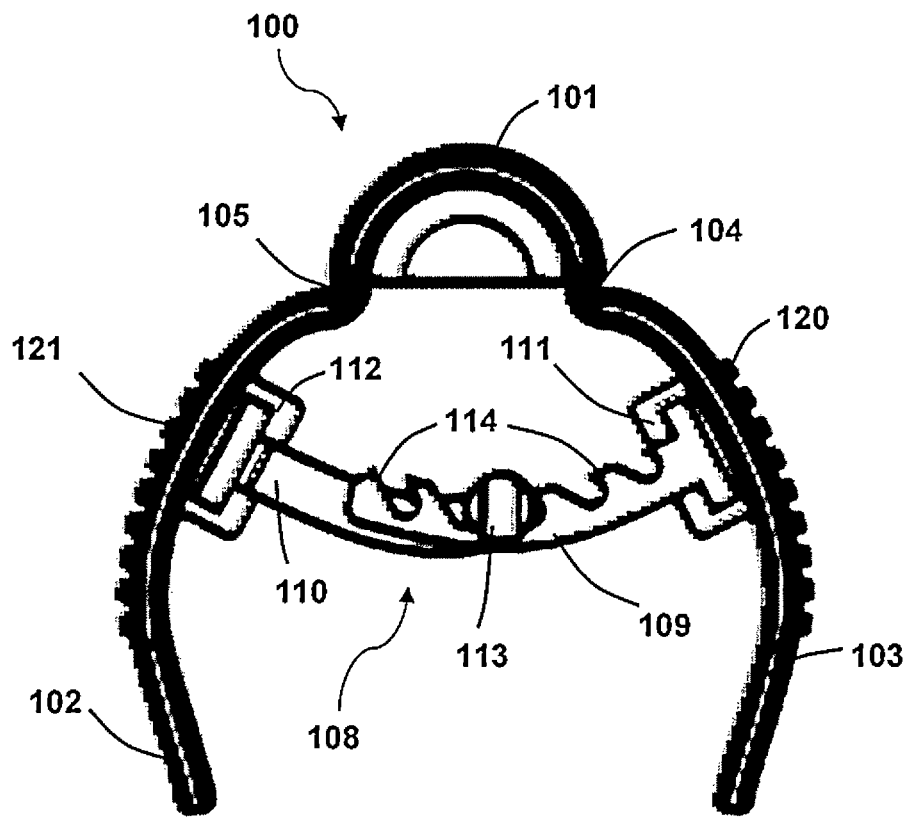
FIG. 4 is a rear view of the exemplary retractor of FIG. 1.

The exemplary device (100) may also comprise a ratchet mechanism (108), as depicted in FIG. 4. This ratchet mechanism (108) may serve to provide structural support to the wings (102, 103) to counteract the force of the vaginal walls on the wings. This structural support may also prevent the hinges (104, 105) from breaking due to the force of the vaginal walls on the wings (102, 103). The ratchet mechanism (108) may also serve to hold the wings (102, 103) in various positions with respect to each other. For example, the user may desire to have the wings (102, 103) closer to each other during insertion and removal of the device (100). Various wing positions may also be desired for different body shapes, sizes, or morphologies.

The ratchet mechanism (108) may comprise ratchet arms (109, 110) that are affixed to the interior surfaces of the wings (102, 103). One ratchet arm (110) may comprise a peg (113) which may be removably interlocked in different positions to various teeth (114) on the other ratchet arm (109). In some embodiments, the ratchet arms (109, 110) may be affixed directly to the wings (102, 103), not shown, while in other embodiments the arms (109, 110) may be affixed to bases (111, 112) that are affixed to the wings (102, 103), as shown in FIG. 4. The bases (111, 112) may provide additional structural support to the wings (102, 103) and may prevent the ratchet arms (109, 110) from breaking off of the wings (102, 103). In some embodiments, the ratchet mechanism (108) may be configured to prevent the wings (102, 103) from moving toward each other from the force of the vaginal walls, while in other embodiments the ratchet mechanism (108) may be configured to lock together to prevent the wings (102, 103) from moving away from each other (due to the configuration of the hinges).

In another exemplary embodiment (not shown), the device (100) may comprise a gripping proximal tip at the proximal end. This gripping proximal tip may extend from the proximal end of the central body portion (101). This gripping proximal tip may stick out of the vagina while the rest of the device is inserted, and thus allow the user to grab the portion to facilitate removal of the device from the body.

Figure 5:
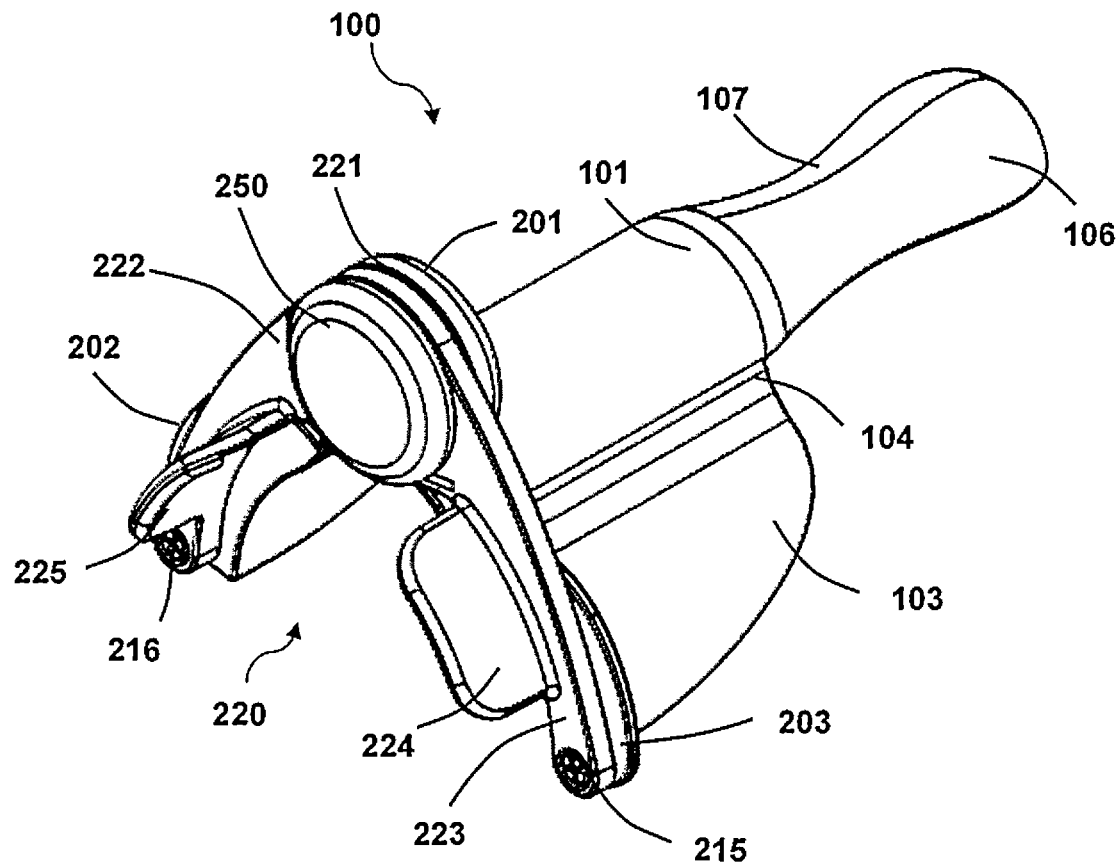
FIG. 5 is an isometric view of another exemplary retractor.
Figure 6:
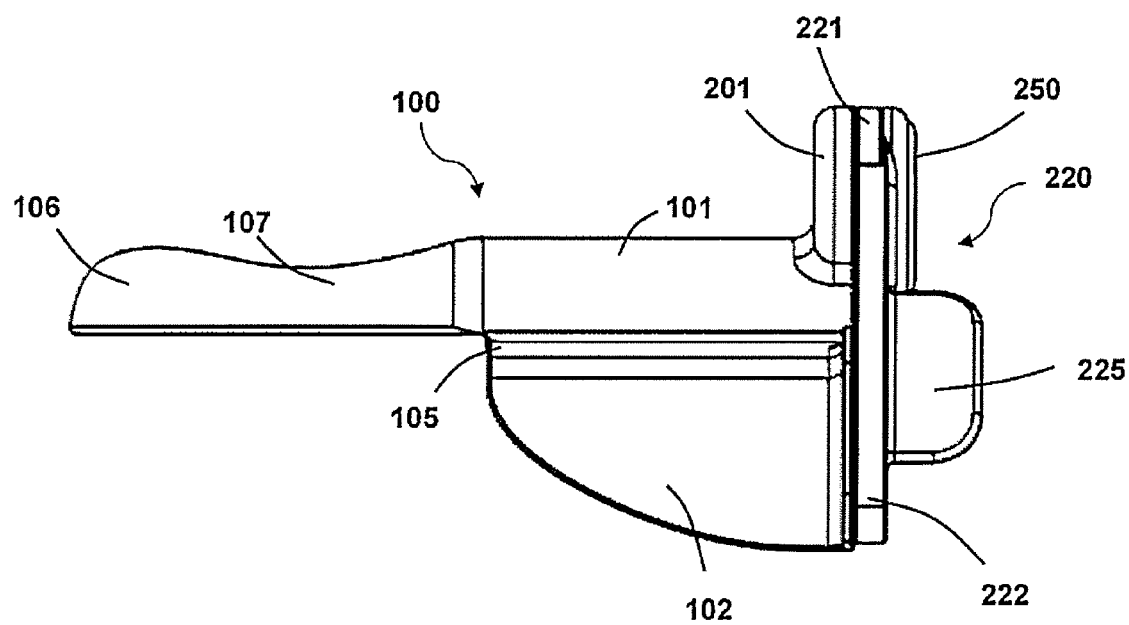
FIG. 6 is a side view of the exemplary retractor of FIG. 5.

FIG. 5 presents an isometric view of another exemplary retractor (100). In this embodiment, the retractor comprises a retractor limiter (201). The limiter (201) may be included in the same molded part as the central body portion (101). The limiter (201), shown from the side in FIG. 6, may prevent the retractor (100) from penetrating too far into vagina, and may prevent damage to the cervix, uterus, or other parts of the female patient. The limiter (201) may also have a smooth surface free of surface protrusions or holes in order to prevent painful interaction with the clitoris.

The wings (102, 103) of FIG. 5 also comprise lips (202, 203) at their proximal ends. The lips (202, 203) along with the wings (102, 103), central body portion (101), and limiter (201) may prevent blood, tissue, or other materials from entering the area where the suturing takes place. The lips (202, 203) may also help to prevent the retractor from penetrating too deeply into the vagina. The lips may also increase stability of the retractor, and help to secure its position with respect to the vagina.

Figure 7:
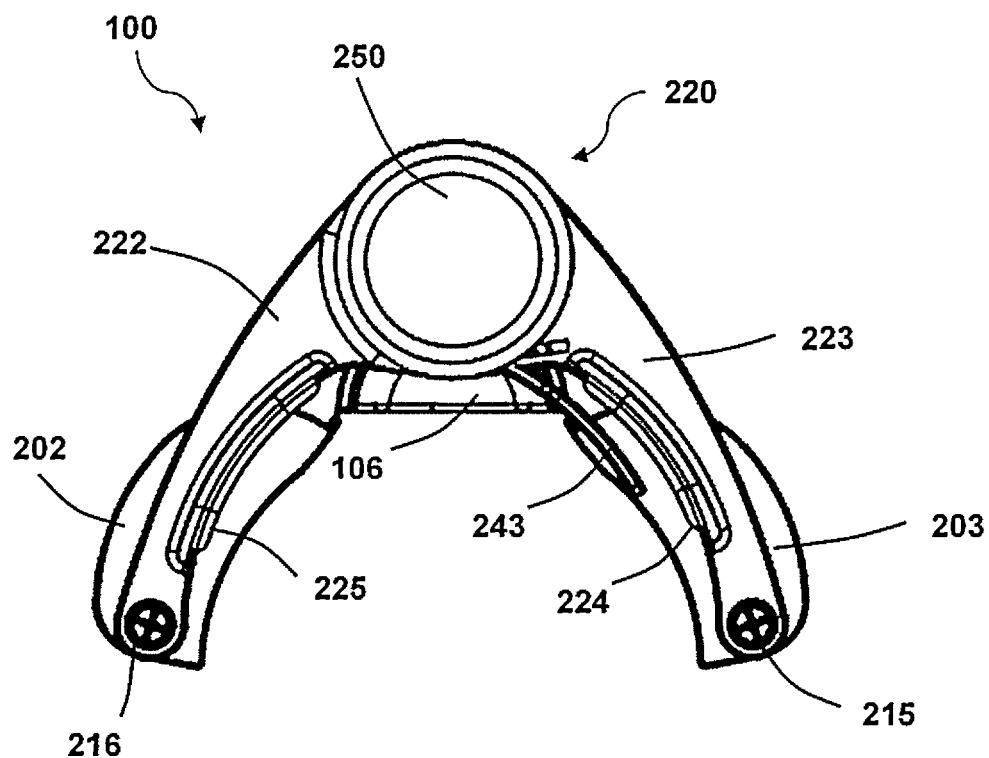
FIG. 7 is a rear view of the exemplary retractor of FIG. 5.
Figure 8:
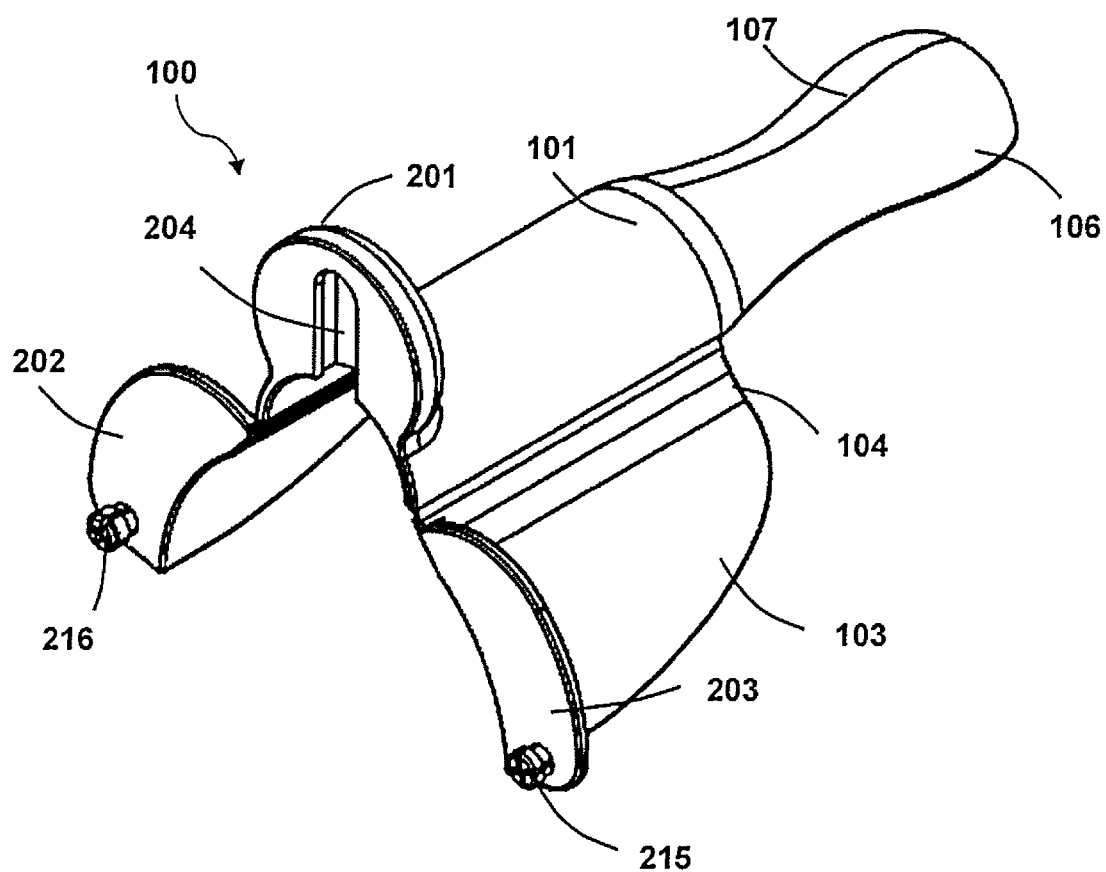
FIG. 8 is an isometric view of the exemplary retractor of FIG. 5 without a ratchet mechanism.

The retractor (100) of FIG. 5 may also comprise a ratchet mechanism (220) comprising two ratchet arms (222, 223), shown straight-on in FIG. 7. As shown in the assembled view of FIG. 5, the ratchet arms (222, 223) may attach to three areas of the retractor body: at the base of each wing lips (202, 203) and at the ratchet hub (221). As shown in FIG. 8, the lips (202, 203) may comprise fasteners (216, 215), which may comprise barbed pins, that engage the fastener recesses (225, 226) of the ratchet arms.

Figure 9:
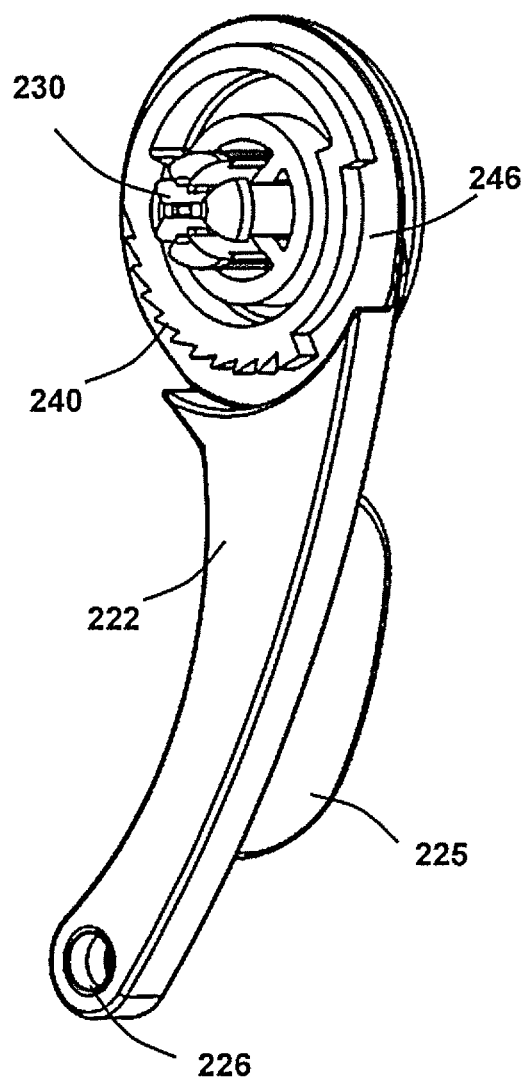
FIG. 9 is a retractor arm of the ratchet mechanism of the exemplary ratchet system of FIG. 5.

The ratchet arms (222, 223) may further attach to the body of the retractor by means of central ratchet hub fastener (230) protruding from the left retractor arm (222), as shown in FIG. 9. The ratchet hub fastener (230) may comprise barbed pins. The ratchet hub fastener pin (230) may pass through a hole (231) shown in FIG. 10.

The ratchet hub fastener pin (230) may also fasten to a limiter recess (204) on the proximal side of the limiter (201), shown in FIG. 8. The limiter recess (204) of FIG. 8 may be elongated along its vertical axis in order to allow the fastener pin (230) to slide up and down along the vertical axis of the limiter. This sliding may be necessary as the ratchet arms (222, 223) move away from each other, since in this embodiment the fasteners (216, 215) are fixed to the lips (202, 203).

In other embodiments, the limiter recess may not be elongated, so that the fastener pin (230) would not move up or down with respect to the limiter (201). Rather, the fastener recesses (225, 226) of the ratchet arms could be elongated so that the fasteners (216, 215) is fixed to the lips (202, 203) and could move along the elongated fastener recesses (225, 226).

As shown in FIG. 5, FIG. 6, FIG. 7, and FIG. 11, the ratchet arms (222, 223) may also comprise ratchet grasps (224, 225). The ratchet grasps may be useful for spreading the ratchet arms away from, or closer to, each other. The ratchet grasps may also be useful for altering the position of the retractor (100), inserting the retractor, or removing the retractor. The ratchet grasps (224, 225) may further comprise textures, or other protruded and/or thinned portions, in order to increase friction and facilitate gripping by the user.

Figure 10:
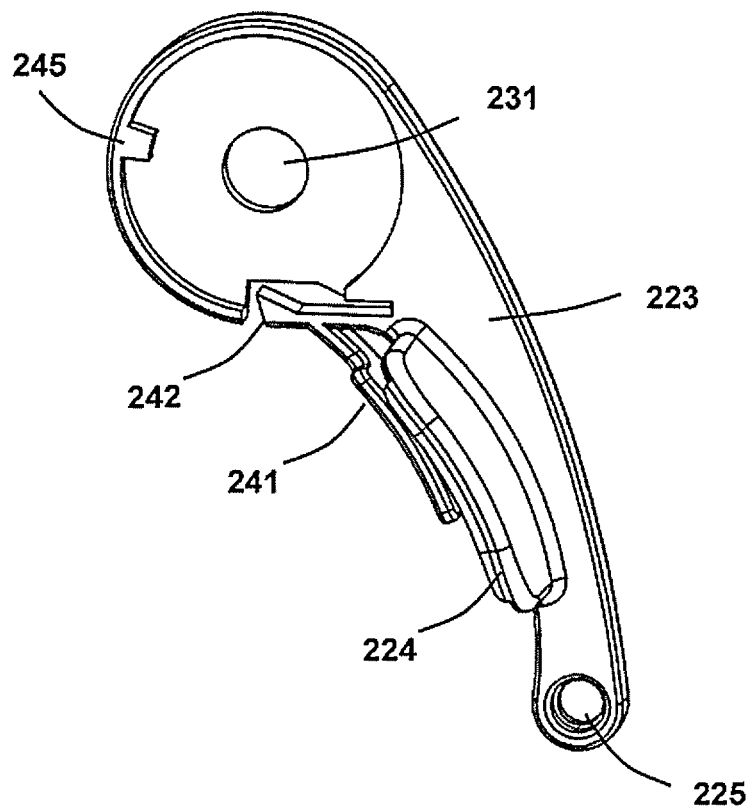
FIG. 10 is another retractor arm of the ratchet mechanism of FIG. 5.

FIGS. 9 and 10 show additional details of the ratchet mechanism (220). FIG. 9 shows the left ratchet arm (222) turned over to show its inner workings. The other ratchet arm (223), shown in FIG. 10, comprises a ratchet release trigger (241) that comprises a ratchet release trigger handle (243) and a ratchet release tooth engager (242). The ratchet release tooth engager (242) may be configured to latch onto the ratchet teeth (240) of the ratchet arm (222) of FIG. 9. The tooth engager (242) may release from the teeth (240) when the user presses the trigger handle (243).

Figure 11:
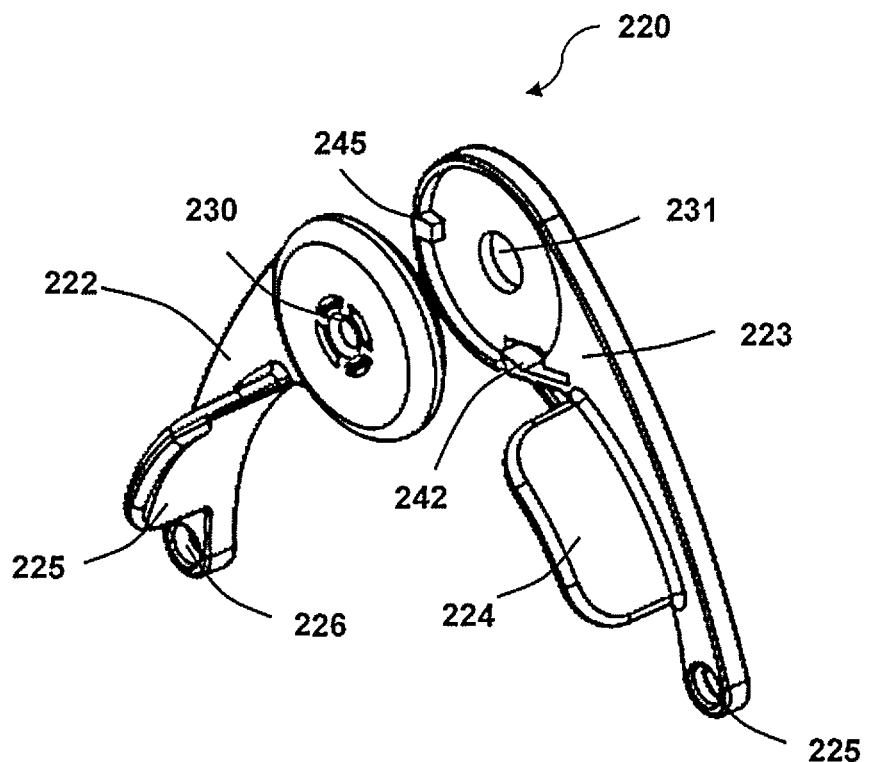
FIG. 11 is an isometric view of separated parts of the ratchet mechanism of the exemplary retractor of FIG. 5.

In FIG. 9, a carve-out to the right of the ratchet teeth (241) may serve as a ratchet limiter engaging slot (246) along which a ratchet limiter stop (245) of FIGS. 10 and 11 may move as the ratchet arms move relative to each other. This may prevent the distance between the bases of the of the ratchet arms (222, 223) from exceeding three inches. In some embodiments, the distance may be more than three inches, for instance four inches. In other embodiments, it may be 2.5 inches or less.

In some embodiments, the retractor may comprise a polymer such as acrylonitrile butadiene styrene (ABS), polyurethane, acetal plastics, or another material known to those skilled in the art that provides both structural rigidity and flexibility. It may comprise flexible plastic material such as polyamide sold under the trade name "NYLON," polytetrafluoroethylene sold under the trademark "TEFLON". Alternatively, a polypropylene plastic or a high density polyethylene plastic may be used to manufacture the retractor. The device may be made of a transparent plastic in order to enhance the viewing area. It may also be made of metal. Mixtures or composites of these materials may also be used to manufacture the minimally obstructive retractor.

The hinge may comprise a polymer. The hinge, for example, may comprise polyethylene, polypropylene, nylon, acetal plastics or mixtures thereof. In another example, the hinge material may even be polyethylene, polypropylene or mixtures thereof.

The retractor may be sterilizable by ethylene oxide, gamma radiation or other process known to those skilled in the art. It may be disposable or reprocessable. Also, the device may be made of different sizes and/or thicknesses to accommodate different ages and sizes of patients. The device may be coated with a material to facilitate inspection and movement. For example, a lubricant can be used to coat the device to facilitate insertion and retrieval.

In one embodiment, the minimally obstructive retractor further comprises an illumination source. The illumination source may comprise more than one illumination devices.

Yet, in a further embodiment, one or all device components forming the illumination source are located within the canopy formed by the retractor. For example, the illumination source may comprise a light-emitting diode wherein the light emitting diode is located within the retractor canopy. Also, in another example, the whole illumination source is located within the retractor canopy. In such embodiments, a compact retractor with no illumination source components dangling beyond the other retractor parts may be obtained.

Figure 12:
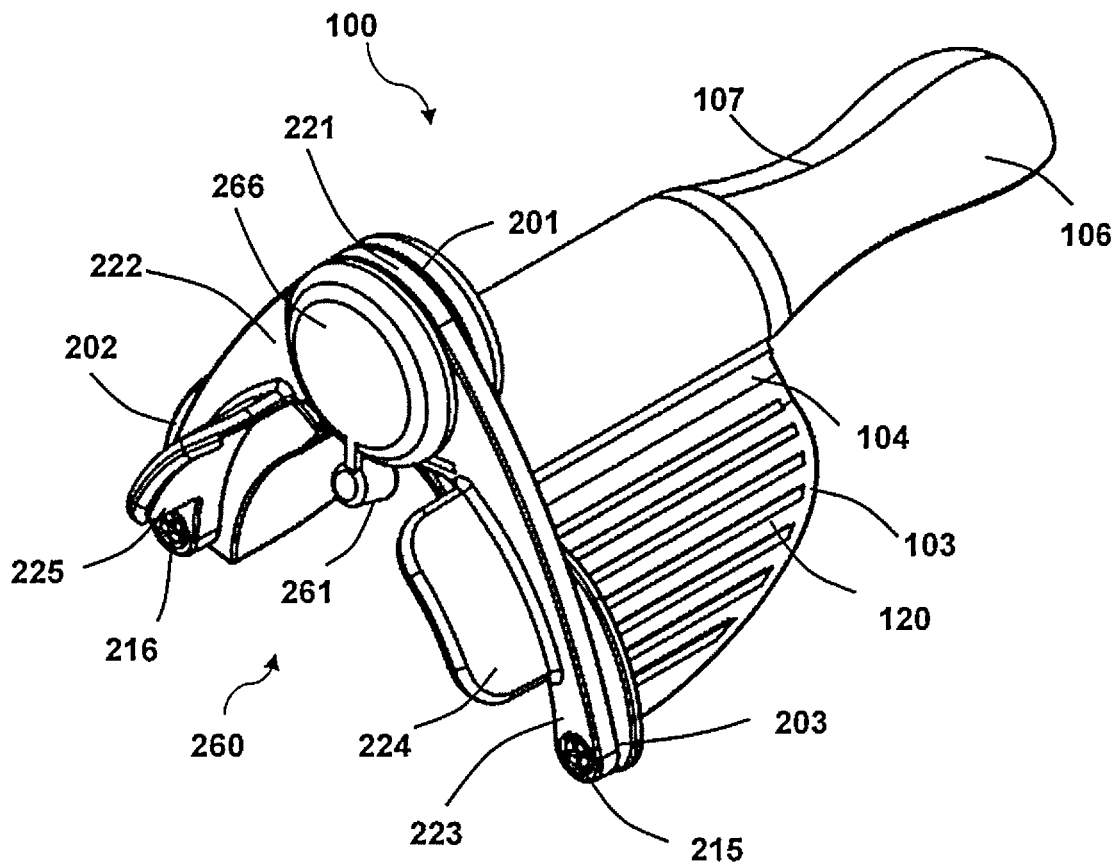
FIG. 12 is an isometric view of another exemplary retractor comprising a light source.
Figure 13:
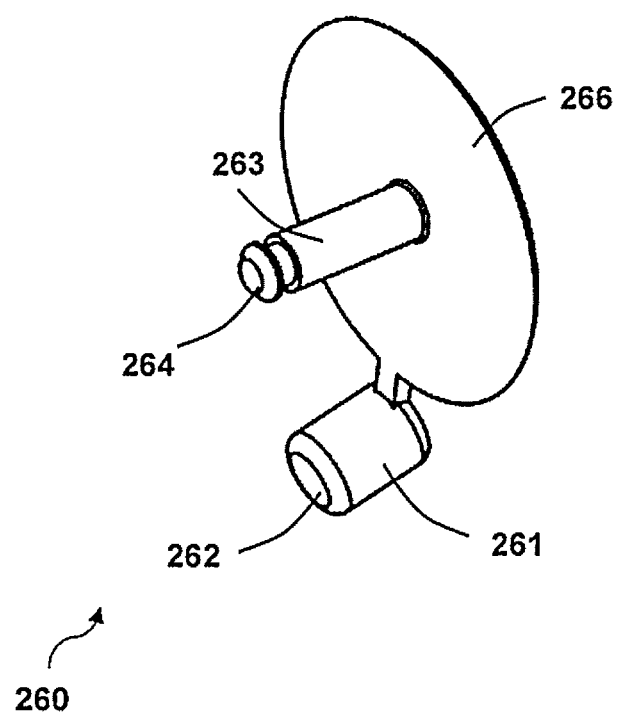
FIG. 13 is a close-up view of a ratchet cap, including a light source, of the exemplary retractor of FIG. 11.
Figure 14:
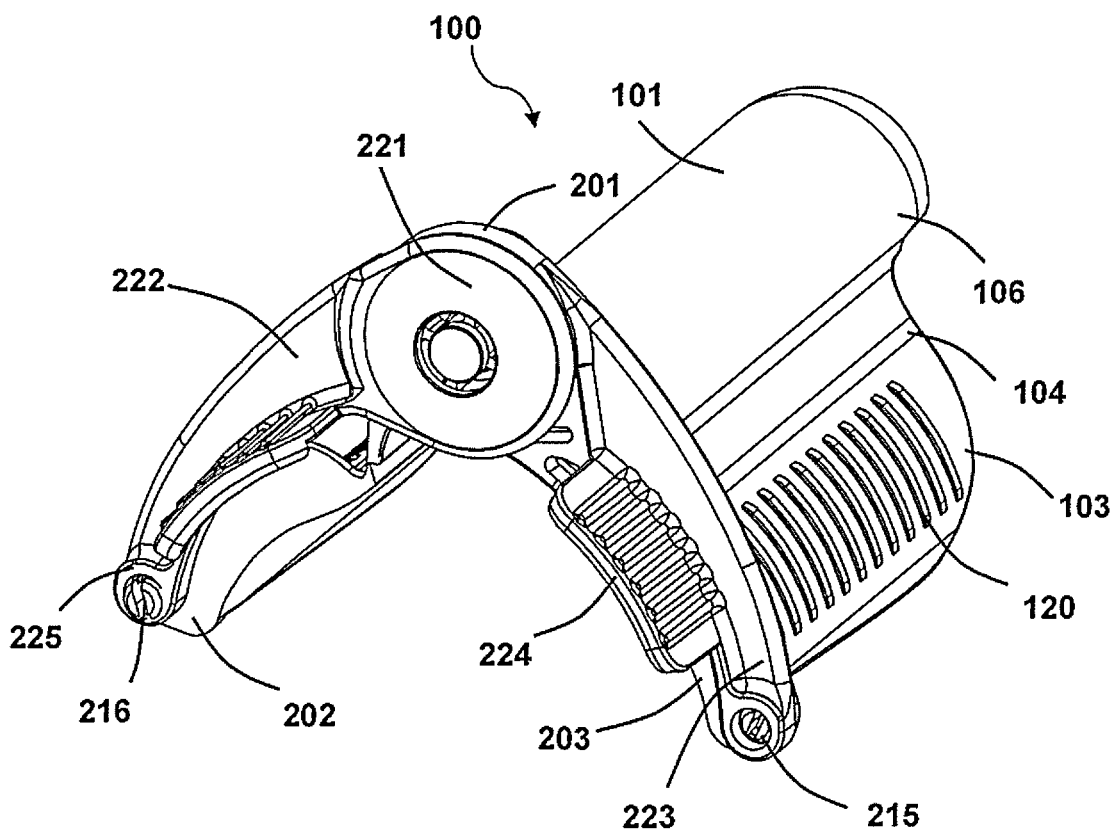
FIG. 14 is an isometric view of an alternative exemplary retractor.

One exemplary embodiment of the minimally obstructive retractor (100) comprising an illumination source (260) is shown in FIG. 12. As shown in FIG. 13, an exemplary illumination source (260) may comprise a light (262), such as battery-powered light-emitting diode (LED), located within a light source housing (261). In the embodiment of FIGS. 12 and 13, the light source housing (261) may be attached to a cap (266) that attaches to the limiter (201) of FIG. 12. The cap (266) may attach to the limiter (201) by means of a fastener (263), comprising a pin (264), which connects to either a ratchet arm or the limiter (201). In some embodiments, the cap (266) does not have a fastener; rather it may attach by means of an adhesive. In some embodiments, the illumination housing (261) may be configured to swivel. In some embodiments the user may manually operate the light function externally via a mechanical switch, while in alternative embodiments, the light function may be turned on and off automatically.

FIGS. 14-17 depict various views of another exemplary retractor with alternative illumination and structural features. The device may comprise a central body portion (101), wings (102, 103) that may be connected to the central body portion (101) via living hinges (104, 105), and a ratchet mechanism (108). The ratchet arms (109, 110) may be assembled together at a ratchet hub (221). For example, a ratchet hub fastener (230) on ratchet arm (222) shown in FIG. 16 may fasten to a limiter recess (204) within a limiter (201) shown in FIG. 15.

Figure 15:
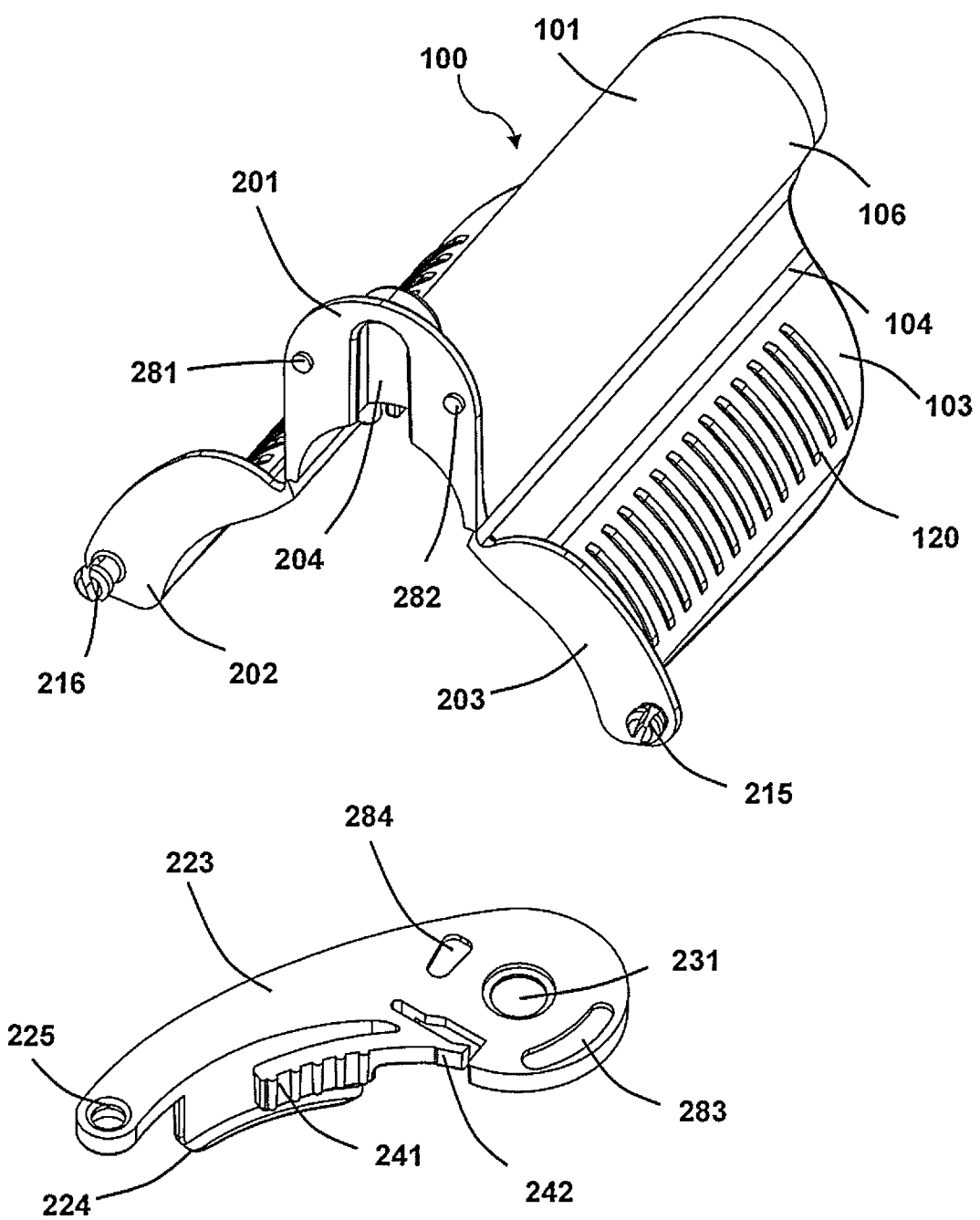
FIG. 15 is an isometric view of separated parts of the exemplary retractor of FIG. 14.

As shown in FIG. 15, to stabilize the sliding motion of the main body relative to the ratchet arms, the central body portion (101) may comprise two pegs (281,282) which are able to travel back and forth within mating grooves (283, 284, respectively) integrated within the ratchet arms (109, 110), thereby effectively restricting rotation of the retractor (100) off axis.

Figure 16:
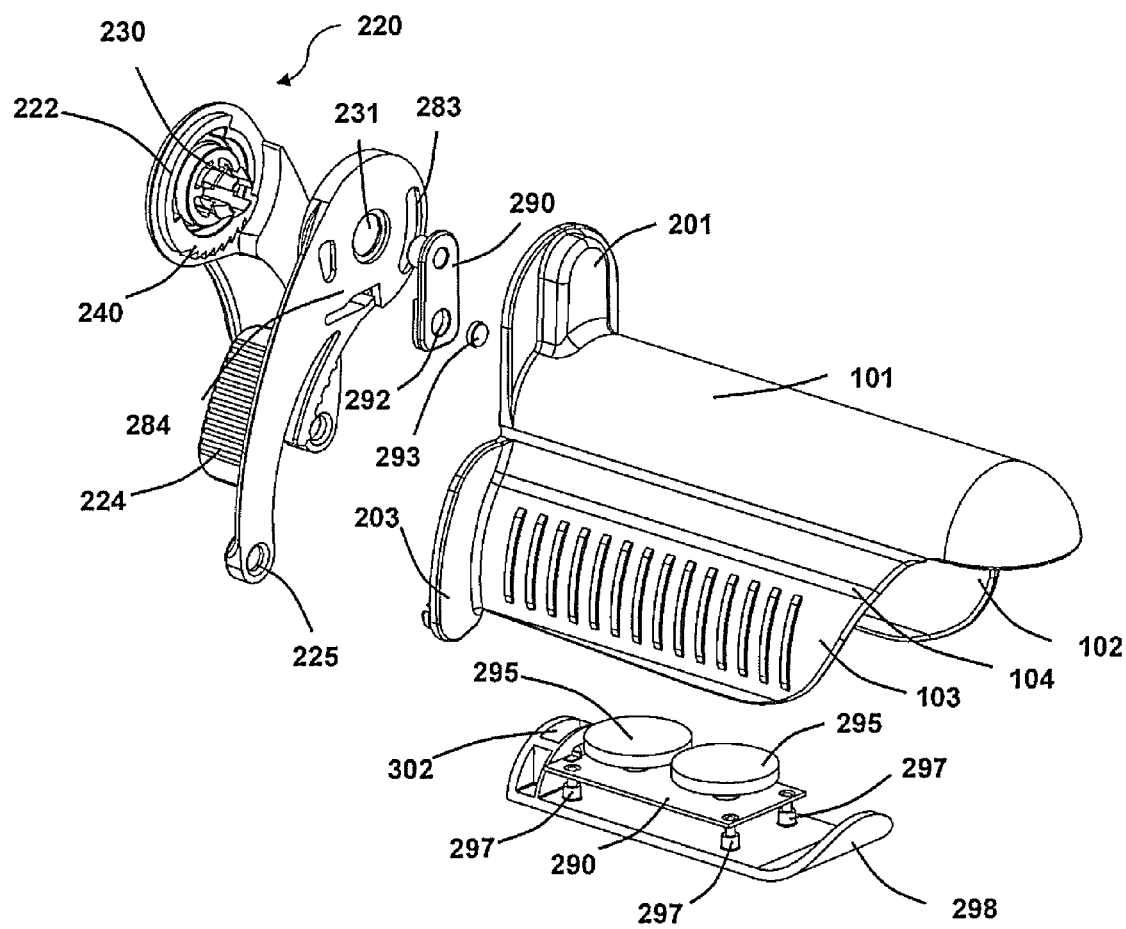
FIG. 16 is an exploded, isometric view of separated parts of the exemplary retractor of FIG. 14.
Figure 17:
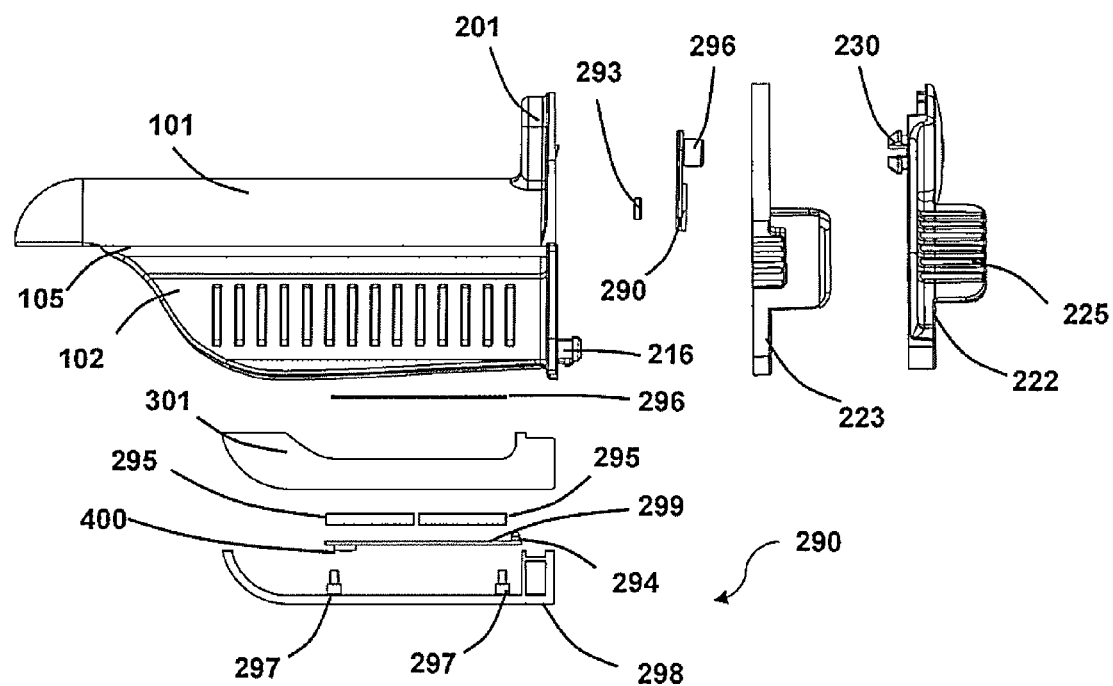
FIG. 17 is an exploded, side view of separated parts of the exemplary retractor of FIG. 14.

As shown in FIGS. 16 and 17, the wings (102, 103) may flare outward along a portion of their length. In particular, distance between the opposing wings may be greater toward the end that is deeper the body cavity, and may be narrower toward the opening of the vaginal cavity. Consequently, pressure of the vaginal walls upon the length of the device's blades may tend to hold the device within the cavity, thereby preventing the device from sliding out of the vagina.

The exemplary embodiment of FIGS. 14 to 17 comprises an alternative embodiment of an illumination source (260). The illumination source (260) may comprise a plurality of light emitting components such as light emitting diodes (LEDs) (400) capable of producing sufficient visible light to view the area of interest, a power supply such as coin cell batteries (295) to drive the LED (400), power management components such as resistors, and reed sensor switch (294) to activate the LED (400). The LED (400), resistors, reed switch (294) and power supply batteries (295) may be assembled on a printed circuit board (299), also known as a PCB.

The exemplary embodiment of FIGS. 14 to 17 further comprises an illumination source that may be automatically turned on and off in conjunction with movement of the ratchet arms away from, and towards, each other, respectively.

In the exploded view of the device in FIG. 17, the LED may be turned on and off via a reed sensor switch (294). The reed sensor switch (294) may be turned on in the presence of a magnetic field generated by a magnet (293), and may turn off in the absence of the magnetic field generated by the magnet. The reed sensor switch (294) may be sensitive to the position of the magnet (293). The magnet (293) may be positioned within a magnet receptacle (292) within the stem (290). The stem (290) may hold the magnet (293) and provide the magnet with a path to actuate the LED assembly by positioning the magnet (293) within close enough proximity to the reed sensor switch (294) to activate the switch (294).

The stem may be assembled between the limiter (201) and the ratchet arms (222, 223). Specifically, the stem (290) may travel along a vertical path within a recess (204) of the limiter (201) as it travels along with the ratchet arms (222, 223) when the ratchet arms are opened and closed to open and close the device wings (102, 103). A stem pin (291) may pass through the hole (231) on ratchet arm (223) and engage with the ratchet hub fastener pin (230) of ratchet arm (222). This engagement between the stem pin (291) and the ratchet hub fastener pin (230) may cause the stem (290) to slide along the limiter recess (204) of the limiter (201).

The coin cell batteries (295) may be connected using contact wires (296) or directly assembled onto the PCB (299). Alternatively, the electronic components may be brought in contact to complete the circuit without soldering and connected by compression of the assembly packaging.

The LED assembly (290) may be placed onto a plurality of mounting posts (297) on an LED cover (298), which may comprise a translucent material, and assembled into mating features (not shown) located on the underside of the central body portion (101).

In FIG. 17, a gasket (301), made of rubber or other materials, may be placed between the LED cover (298) and an inner surface of the central body portion (101) to prevent or minimize the ingress of fluids and dirt into the LED assembly (290). In addition, in the case of leaking power supply batteries, the gasket (301) may prevent chemicals from leaking outside the device, thereby protecting the user. The gasket (301) may be held in place by mating features in the main body surface, by adhesive, or by other means.

The LED cover (298) and LED assembly (298) may also be mated with the main body via other fastening mechanisms such as screws or epoxy.

The stem may travel in a vertical path inside a slot (302) located with the LED cover (298), thereby making the actuation mechanism hidden from to the user.

In another embodiment (not shown), the mechanism of turning the light on and off may comprise a mechanical push button switch. The switch may be placed behind the ratchet arms at a location where the arms interact with each other. When the ratchet arms are opened outward and pass over each other, the switch may be triggered, thus completing the electrical circuit and turning on the light.

In another embodiment, the mechanical push button switch may be placed between the ratchet arm surfaces where the mechanical push switch button may by pressed in the off position when the ratchet arms are closed, thus keeping the light function off. When the ratchet arms are opened outwardly, this may release the switch, thereby turning the switch to the on position, completing the electrical circuit and turning the light function on.

Alternatively, the mechanical push button switch may be accessible to the user to manually turn the light function on or off. The switch may be located on the ratchet arm hub for easy access.

In another embodiment, an optical sensor switch may be used to activate the light function. The switch may be placed in the main body or ratchet arm and between the surfaces thereby occluding the sensor of the switch from ambient light. When the ratchet arms pass over and expose the optical sensor, the switch turns the light function on.

In another embodiment, a breakoff plastic feature may be used to trigger a switch (or an incomplete circuit by a separated wire connection) to turn on the light. In the closed position, one of the ratchet arms may be connected to the switch via a plastic feature or tab. When the ratchet arms are pulled outward to open the wings, this plastic tab could break, consequently activating the switch (or completing the connection between the separated wire) to turn on the light. With this mechanism, the device light function could stay on until the batteries are drained of their power. A variation of this mechanism may use the plastic tab as a cover over the optical sensor switch. On pulling the ratchet arms outwardly, the plastic tab could break and expose the optical sensor, thereby completing the electrical circuit and turning the light on.

In other embodiments, the device may comprise a plurality of LEDs located at various portions of the interior of the device. For example, the LEDs may be located on or integrated within the interior surfaces of the central body portion (101), the distal tip (106), and/or the wings (102, 103).

In some exemplary embodiments, the retractor may comprise a lubrication source. This lubrication source may comprise a lubricant-containing reservoir integrated with the body of the device, and a channel for delivering the biocompatible lubricant. For example, the reservoir may be located on, or integrated within, the interior surfaces of the central body portion (101), the distal tip (106), and/or the wings (102, 103). The channels may provide lubrication to the outer surfaces of the retractor (100).

In some embodiments, a significant portion of the device (100) may be formed from a single continuous material. That is, the retractor—is formed from only one component. In these embodiments, the retractor may be manufactured by molding. For example, in an exemplary embodiment, the central body portion (101), wings (102, 103), and distal tip (106) may be injection molded to form a single component. An exemplary material for injection molding may be polypropylene.

The device (100) may be used in various procedures, including episiotomy repair, repair of vaginal lacerations, and visualization during checkups. For example, the ratchet mechanism (220) may be adjusted to hold the wings (102, 103) in various positions with respect to each other. For example, the user may desire to have the wings (102, 103) closer to each other during insertion and removal of the device (100), while keeping the wings (102, 103) farther apart from each other to maximize the viewing and working fields during procedures. Various positions may also be desired for different body shapes, sizes, or morphologies. The position of the wings may be changed during procedures using the ratchet mechanism (220).

The device may be used for improved visualization, access, and repair in various procedures, including, but not limited to: obstetrical/gynecological procedures: vaginal inspection; perineal inspection; vaginal wound repair; perineal wound repair; episiotomy repair; female pelvic exam; pap smear; cervical biopsy; vaginal/pelvic reconstruction; urological procedures; colorectal, general, or other surgery; the device may be turned upside-down, for example, for female urologic procedures; access to the cervix (or uterus via cervix); IUD insertion, removal, or adjustment; and dilatation & curettage (dilatation of cervix and curettage of uterus).

The previous description of embodiments is provided to enable any person skilled in the art to make or use the retractors and speculums. Various modifications to these embodiments will be readily apparent to those skilled in the art, and the generic principles defined herein may be applied to other embodiments without departing from the spirit or scope of the retractors and speculums. Thus, the retractors and speculums are not intended to be limited to the embodiments shown herein but are to be accorded the widest scope consistent with the principles and novel features disclosed herein.

We claim:

1. A minimally obstructive retractor having a proximal end, a distal end, an exterior surface, and an interior surface, comprising:
   a central body portion;
   at least two wings;
   at least two hinges, each configured to affix a different one of the at least two wings to the central body portion, the wings being rotatable about the hinges when moving from a closed to an open position, wherein the wings, the hinges, and the central body portion form a canopy that creates and only partially surrounds an interior space that is not surrounded by any other portion of the retractor when the wings are in the open position, wherein no portion of the retractor obstructs any portion of a length of the interior space opposite the central body portion between the proximal end and the distal end when the wings are in the open position; and a rachet mechanism that releasably locks the wings in an open position.

2. The minimally obstructive retractor of claim 1, wherein the at least two hinges are living hinges.

3. The minimally obstructive retractor of claim 1, further comprising thinned portions, protrusions, or combinations thereof, on the exterior surface of the central body portion, one of the wings, or both the central body portion and the wings.

4. The minimally obstructive retractor of claim 1, wherein the ratchet mechanism comprises at least one arm that is affixed to an interior surface of at least one of the wings.

5. The minimally obstructive retractor of claim 4, wherein the ratchet mechanism is configured to open and close.

6. The minimally obstructive retractor of claim 4, wherein the retractor further comprises a magnet and a stem; and wherein the stem is configured to hold the magnet and is further configured to travel along a vertical path when the ratchet arm is opened and closed.

7. The minimally obstructive retractor of claim 4, wherein the retractor further comprises two mating grooves, which are integrated within the ratchet mechanism, and two pegs; and wherein the two mating grooves and the two pegs are configured to effectively restrict rotation of the retractor off axis.

8. The minimally obstructive retractor of claim 4, wherein the ratchet mechanism further comprises a central ratchet hub fastener configured to attach to the central body portion of the retractor.

9. The minimally obstructive retractor of claim 1, further comprising a gripping proximal tip at the proximal end.

10. The minimally obstructive retractor of claim 1, further comprising a retractor limiter at the proximal end.

11. The minimally obstructive retractor of claim 7, wherein the limiter further comprises a recess.

12. The minimally obstructive retractor of claim 11, wherein the retractor further comprises a magnet and a stem; and wherein the stem is configured to hold the magnet and is further configured to travel along a vertical path within the recess of the limiter when the wings are moved between the open and closed positions.

13. The minimally obstructive retractor of claim 11, wherein the retractor further comprises a ratchet mechanism comprising at least one arm that is affixed to an interior surface of at least one wing; wherein the ratchet mechanism further comprises a central ratchet hub fastener configured to attach to the central body portion of the retractor; and wherein the limiter recess is configured to allow the central ratchet hub fastener to slide up and down along the vertical axis of the limiter.

14. The minimally obstructive retractor of claim 13, wherein the retractor mechanism further comprises two mating grooves, which are integrated within the ratchet mechanism, and two pegs; and wherein the two mating grooves and the two pegs are configured to effectively restrict rotation of the retractor off axis.

15. The minimally obstructive retractor of claim 1, further comprising an illumination source comprising at least one light-emitting diode.

16. The minimally obstructive retractor of claim 15, wherein the at least one light-emitting diode is located within the canopy.

17. The minimally obstructive retractor of claim 15, wherein the illumination source is automatically turned on in conjunction with movement of ratchet arms away from each other or automatically turned off in conjunction with movement of the ratchet arms towards each other.

18. The minimally obstructive retractor of claim 15, further comprising an illumination source, wherein the illumination source is located within the canopy.

19. The minimally obstructive retractor of claim 1, wherein the hinges comprise polyethylene, polypropylene, nylon, acetal plastics or a mixture thereof.

20. The minimally obstructive retractor of claim 1, wherein the hinges comprise polyethylene, polypropylene, or a mixture thereof.

21. The minimally obstructive retractor of claim 1 wherein the retractor further comprises a lubrication source comprising a lubricant-containing reservoir integrated to the retractor and configured to provide lubricant to an outer surface of the retractor.

22. The minimally obstructive retractor of claim 1, wherein the retractor further comprises a magnet and a stem; and wherein the stem is configured to hold the magnet and is further configured to travel along a vertical path.

23. The minimally obstructive retractor of claim 1, wherein the retractor further comprises a magnet and a stem; and wherein the stem is configured to hold the magnet and is further configured to travel along a vertical path while the wings are moved between the open and closed positions.

24. The minimally obstructive retractor of claim 1, wherein the retractor further comprises two pegs and two mating grooves that are configured to effectively restrict rotation of the retractor off axis.

25. The minimally obstructive retractor of claim 1, wherein the mechanism further comprises two ratchet arms.

26. The minimally obstructive retractor of claim 25, wherein the wings and the ratchet mechanism can move away from or closer to each other.

27. The minimally obstructive retractor of claim 26, wherein the ratchet mechanism further comprises a central ratchet hub fastener.

28. The minimally obstructive retractor of claim 27, further comprising a retractor limiter at the proximal end.

29. The minimally obstructive retractor of claim 28, wherein the limiter further comprises a limiter recess.

30. The minimally obstructive retractor of claim 29, wherein the limiter recess is configured to allow the central ratchet hub fastener to slide up and down along a vertical axis of the limiter.

31. The minimally obstructive retractor of claim 30 . . . , wherein the retractor further comprises two pegs and two mating grooves.

32. The minimally obstructive retractor of claim 31, wherein the two mating grooves are integrated within the ratchet mechanism.

33. The minimally obstructive retractor of claim 26, wherein the retractor further comprises an illumination source; wherein the illumination source is attached to the limiter.

34. The minimally obstructive retractor of claim 27, wherein each wing further comprises a lip at its proximal end.

35. The minimally obstructive retractor of claim 34, wherein each lip further comprises a fastener.

36. The minimally obstructive retractor of claim 35, wherein each ratchet arm further comprises at least one elongated fastener recess.

37. The minimally obstructive retractor of claim 26, further comprising an illumination source.

38. The minimally obstructive retractor of claim 37, wherein the illumination source is located within the canopy.

39. The minimally obstructive retractor of claim 37, wherein the illumination source is configured to automatically turn on in conjunction with movement of the ratchet arms away from each other or automatically turn off in conjunction with movement of the ratchet arms towards each other.

40. The minimally obstructive retractor of claim 39, wherein the retractor further comprises a reed sensor switch and a magnet.

41. The minimally obstructive retractor of claim 26, wherein each wing further comprises a lip at its proximal end.

42. The minimally obstructive retractor of claim 25, wherein the wings comprise serrated wing edges.

43. The minimally obstructive retractor of claim 25, further comprising thinned portions, protrusions, or combinations thereof, on the exterior surface of the central body portion, the wings, or both the central body portion and the wings.

44. The minimally obstructive retractor of claim 25, wherein the at least two hinges are living hinges.

45. The minimally obstructive retractor of claim 1, wherein the wings comprise serrated wing edges.

46. The minimally obstructive retractor of claim 1, wherein the canopy substantially blocks fluid flow through the exterior surface of the canopy.

47. The minimally obstructive retractor of claim 1, wherein the central body portion and the at least two wings constitute a single continuous component.

48. The minimally obstructive retractor of claim 47, further comprising at least one ratchet mechanism.

49. The minimally obstructive retractor of claim 48, wherein the at least one ratchet mechanism comprises two ratchet arms.

50. The minimally obstructive retractor of claim 49, wherein the wings and the ratchet mechanism can move away from or closer to each other.

51. The minimally obstructive retractor of claim 1, wherein the minimally obstructive retractor includes only one central body portion, only two wings, and only two hinges.

52. The minimally obstructive retractor of claim 1, wherein each wing has an edge that is not connected to any other portion of the retractor.

53. The minimally obstructive retractor of claim 1, wherein:
  the retractor has a direction of insertion;
  each wing has a lateral edge that is substantially parallel to the direction of insertion; and
  each hinge is connected to the lateral edge of a different one of the wings.

* * * * *